United States Patent
Karni et al.

(10) Patent No.: US 8,150,532 B2
(45) Date of Patent: *Apr. 3, 2012

(54) SYSTEM AND METHOD FOR HEATING BIOLOGICAL TISSUE VIA RF ENERGY

(75) Inventors: Ziv Karni, Kfar Shmaryahu (IL); Alexander Britva, Migdal Haemek (IL)

(73) Assignee: Alma Lasers Ltd., Caesarea (IL)

( * ) Notice: Subject to any disclaimer, the term of this patent is extended or adjusted under 35 U.S.C. 154(b) by 53 days.

This patent is subject to a terminal disclaimer.

(21) Appl. No.: 12/488,566

(22) Filed: Jun. 21, 2009

(65) Prior Publication Data

US 2009/0326528 A1    Dec. 31, 2009

Related U.S. Application Data

(63) Continuation of application No. 10/562,135, filed as application No. PCT/IL2005/000314 on Mar. 17, 2005, now Pat. No. 7,630,774.

(60) Provisional application No. 60/644,037, filed on Jan. 18, 2005.

(51) Int. Cl.
*A61B 18/18* (2006.01)
*A61B 18/00* (2006.01)

(52) U.S. Cl. ............ 607/101; 607/100; 607/102; 600/9; 600/10

(58) Field of Classification Search .................. 607/100, 607/101, 102; 600/9, 10
See application file for complete search history.

(56) References Cited

U.S. PATENT DOCUMENTS

| | | | |
|---|---|---|---|
| 662,054 A | 11/1900 | Burrow | |
| 3,903,891 A | 9/1975 | Brayshaw | |
| 4,140,130 A | 2/1979 | Storm, III | |
| 4,210,152 A | 7/1980 | Berry | |
| 4,589,423 A | 5/1986 | Turner | |
| 4,674,481 A * | 6/1987 | Boddie et al. | 600/10 |
| 4,798,215 A | 1/1989 | Turner | |
| 4,901,719 A | 2/1990 | Trenconsky et al. | |
| 4,901,720 A | 2/1990 | Bertrand | |
| 5,038,780 A | 8/1991 | Boetzkes | |
| 5,097,844 A | 3/1992 | Turner | |
| 5,143,063 A | 9/1992 | Fellner | |
| 5,186,181 A * | 2/1993 | Franconi et al. | 607/156 |
| 5,324,314 A * | 6/1994 | Boetzkes | 607/51 |
| 5,370,644 A * | 12/1994 | Langberg | 606/33 |
| 5,458,596 A | 10/1995 | Lax et al. | |

(Continued)

FOREIGN PATENT DOCUMENTS

CA    1228401    10/1987
(Continued)

OTHER PUBLICATIONS

Christopher E.M. Griffiths, et al. "Restoration of Collagen Formation in Photodamaged Human Skin by Tretinoin ( Retinoic Acid)," New England J. Med, 329: 530-535 (Aug. 19, 1993).

(Continued)

*Primary Examiner* — Roy Gibson
*Assistant Examiner* — Kaitlyn Smith

(57) ABSTRACT

A system 30 and method(s) 100 for thermal treatment of a selected target within a subject is disclosed. System 30 includes RF source 10, phase shifter 14, impedance matching network 11 and resonator 13. Stationary water molecules 1, such as those in fat cells, are heated. The invention is useful in selective heating of cellulite bodies as a means of treating cellulite.

37 Claims, 5 Drawing Sheets

U.S. PATENT DOCUMENTS

| | | | |
|---|---|---|---|
| 5,484,432 A | 1/1996 | Sand | |
| 5,507,790 A | 4/1996 | Weiss | |
| 5,669,907 A | 9/1997 | Platt et al. | |
| 5,712,605 A * | 1/1998 | Flory et al. | 333/219.1 |
| 5,755,753 A | 5/1998 | Knowlton | |
| 5,919,219 A | 7/1999 | Knowlton | |
| 6,013,075 A | 1/2000 | Avramenko et al. | |
| 6,047,215 A | 4/2000 | McClure et al. | |
| 6,099,523 A | 8/2000 | Kim et al. | |
| 6,131,386 A * | 10/2000 | Trumble | 60/274 |
| 6,163,726 A * | 12/2000 | Wolf | 607/101 |
| 6,203,850 B1 | 3/2001 | Nomura | |
| 6,387,088 B1 | 5/2002 | Shattuck et al. | |
| 6,690,976 B2 | 2/2004 | Fenn et al. | |
| 6,958,063 B1 | 10/2005 | Soll et al. | |
| 7,182,762 B2 | 2/2007 | Bortkiewicz | |
| 7,608,839 B2 | 10/2009 | Coulombe et al. | |
| 2001/0034519 A1 | 10/2001 | Goble | |
| 2002/0043520 A1 | 4/2002 | Bernabei | |
| 2003/0130653 A1 | 7/2003 | Sixto et al. | |
| 2004/0002705 A1 | 1/2004 | Knowlton et al. | |
| 2004/0030332 A1 | 2/2004 | Knowlton et al. | |
| 2004/0116918 A1 | 6/2004 | Konesky | |
| 2004/0186470 A1 | 9/2004 | Goble et al. | |
| 2004/0210282 A1* | 10/2004 | Flock et al. | 607/96 |
| 2005/0173383 A1 | 8/2005 | Coccio et al. | |
| 2006/0189976 A1* | 8/2006 | Karni et al. | 606/41 |
| 2007/0106349 A1* | 5/2007 | Karni et al. | 607/101 |

FOREIGN PATENT DOCUMENTS

| | | |
|---|---|---|
| EP | 1090598 | 4/2001 |
| GB | 1222243 | 2/1971 |
| JP | S63 305863 A | 12/1988 |
| JP | H03-054659 U | 5/1991 |
| JP | 02-201315 | 3/1992 |
| JP | 05-94961 | 10/1994 |
| WO | WO9900144 | 1/1999 |
| WO | WO0230308 | 4/2002 |
| WO | WO2004047659 | 6/2004 |

OTHER PUBLICATIONS

Ilaria Ghersetich, "Ultrastructural Study of Hyaluronic Acid Before and After the Use of a Pulsed Electromagnetic Field, Electrorydesis, in the Treatment of Wrinkles," Int'l J. Dermatol, 33:661-662 (1994).
International PCT Search Report—WIPO—parent PCT.
International PCT Search Opinion—WIPO—parent PCT.
EPO supplementary search report for parallel foreign case sent Aug 11, 2007.
Office Action in EPO for parallel foreign case sent May 10, 2007.
Office Action in EPO for parallel foreign case sent Jul. 25, 2008.
Office Action in EPO for parallel foreign case sent Aug. 19, 2009.
Office Action in Israel for parallel foreign case sent Mar. 18, 2009.
Office Action in Israel for parallel foreign case sent Sep. 19, 2010.
Office Action in Canada for parallel foreign case sent Jul. 15, 2010.
Office Action in Japan for parallel foreign case sent Dec. 6, 2010.
Office Action in Japan for parallel foreign case sent Mar. 7, 2011.
Office Action in Korea for parallel foreign case sent Mar. 29, 2007.
Office Action in Korea for parallel foreign case sent Sep. 28, 2007.
Office Action in Korea for parallel foreign case sent Mar. 24, 2008.
U.S. Appl. No. 11/333,308.
EP1715810 (Parallel EPO application): communication of intention to grant a European patent (Sep. 9, 2011).
Response to EPO office action for EP1715810 (parallel EPO application), filed on Jun. 2, 2010.
Parallel JP application: summary of office communication received Aug. 18, 2011.

* cited by examiner

SYSTEM AND METHOD FOR HEATING BIOLOGICAL TISSUE VIA RF ENERGY

CROSS-REFERENCE TO RELATED APPLICATIONS

This patent application is continuation of U.S. patent application Ser. No. 10/562,135 now U.S. Pat. No. 7,630,774 filed on Dec. 23, 2005, and claims priority from PCT/IL05/000314 filed on Mar. 17, 2005 and from U.S. Provisional Patent Application 60/644,037 filed on Jan. 18, 2005, all of which are hereby incorporated in their entirety by reference.

FIELD AND BACKGROUND OF THE INVENTION

The present invention relates to an improved system and method for heating biological tissue via RF energy and, more particularly, to a system and method which rely upon a single electrode. Control of phase and pulse width modulation of applied RF waves obviates the need for cooling of the skin surface, to facilitate efficient heating of underlying layers of tissue such as dermis and subcutaneous layers. Specifically, heating and contraction of adipose tissues as a means of cellulite reduction is achieved.

Adipose tissues, particularly cellulite, are typically treatable only with a strict regimen of diet and exercise. Patient compliance with these previously available regimens is poor. Cellulite occurs when fat cells swell compressing the flow of blood and lymph. This leads to build-up of fluid and toxins. Connective tissue forms hard fibrous capsules around the fat cells. This results in a "lumpy" appearance. The fat cells involved are located primarily in the third and most deep (skin) layer, which has a variable by thickness depending on the amount fat in the subject. Thickness of this layer typically increases in areas such as abdomen, thighs and buttocks.

Previously proposed methods for cellulite treatment include Topical treatment, Teas and capsules, Cellulite wraps, Endermologie, Mesotherapy, Acthyderm and Ultrasonic and particularly focused ultrasonic treatment. These techniques have demonstrated various degrees of clinical efficacy in reducing the "lumpy" appearance associated with cellulite deposits. In addition, thermotherapy using electromagnetic radiation or radio-frequency (RF) waves has been proposed. RF treatment is more effective than other available therapy regimens since it permits the body to heal itself. Non-invasive electromagnetic radiation, including radio-frequency waves, has been proposed in the prior art for treatment of fat and cellulite in addition to use for contraction of collagen, such as involved in the treatment of wrinkles.

The typical RF technique for heating of biological tissues involves exposing the tissue to RF voltage, which produces RF conductive current through the tissue at a level sufficient to overcome the tissue resistance. The current heats the tissue. This method causes uneven heat accompanied by burning of the outer layer(s) the skin. As a result, many of the conventional systems for implementation of this method share, as an inherent disadvantage, a strict requirement for a cooling mechanism to remove an excessive heat of the skin during the treatment.

One example of a prior art system(s) is disclosed in U.S. Pat. No. 6,662,054 assigned to Syneron Medical Ltd. This patent teaches deforming the skin so that a region of skin protrudes from the surrounding skin, and applying RF energy to the protruded skin. The system includes one or more RF electrodes, configured to apply conducted RF current to the skin, and a skin deformer, so that a region of skin protrudes out from surrounding skin and is exposed to the conducted RF current, which follows the deforming act. Teachings of this include a strict requirement for cooling of the skin to prevent burning.

US Patent Application No. 20040002705 assigned to Thermage, Inc. also discloses a system that requires cooling of skin to prevent burning. In particular, this published patent application teaches a method of creating a tissue effect by delivering electromagnetic energy through a skin surface from an electromagnetic energy delivery device coupled to an electromagnetic energy source.

Further additional examples of prior art systems which require cooling of the skin to prevent burning include those disclosed in US Patent Application No. 2004030332 and U.S. Pat. No. 5,919,219 assigned to Thermage, Inc., which teach a system and method for providing treatment to a skin surface by applying RF energy through the skin using a memory for gathering information. These systems include express requirements for a cooling lumen for receiving cooling fluid and a number of RF electrodes. The RF electrodes are provided to transfer RF current to the skin and are configured to be capacitive coupled to the skin surface, thus creating a heating effect through RF conducted current.

In summary, the above-described prior art methods require the use of a separate cooling system to cool the outer skin layer throughout the RF treatment. Further, many of the previously available solutions require a memory unit to store local information pertaining to the treated area throughout the treatment. Further, many of the previously available solutions require extensive preliminary adjustments, such as local impedance matching, prior to each treatment. Further, despite use of the phrase "one or more electrodes in many prior art documents, the above-described alternatives share, a strict requirement for a return electrode pad to be placed against the patient to receive the RF currents after passing tissue being treated. This return electrode for volumetric treatment of adipose tissue (e.g. cellulite) routes a majority of energy through blood and lymphatic vessels. Fat cells are heated only by heat dissipated from these non-target tissues as a result of their inherent resistance.

There is thus a widely recognized need for, and it would be highly advantageous to have, an improved system and method for heating biological tissue via RF energy that attempts to address one or more of the limitations of the above-described systems.

SUMMARY OF THE INVENTION

According to one aspect of the present invention there is provided a system for RF (HF) energy treatment of deep layers of human tissue (e.g. dermis and/or hypodermis) to achieve adipose tissue contraction and/or cellulite reduction.

The system includes an RF-energy applicator (e.g. spherical shape) which serves as RF-energy coupling antenna that functions in combination with an adjacent tissue as a losses transmission line when contacted with epidermis of the tissue.

The system further includes a treated area (part) of human tissue placed in direct contact with RF-energy applicator whereas underlying subcutaneous tissues acts as a dissipative load of the said applicator and the transmission line.

The system further includes a parallel resonance circuit (RF-resonator) including inductor and capacitor and maximally closely contacted with the said applicator by its central point whereas merit factor of this resonant circuit must be sufficiently high that provides active losses determined by equivalent resistance, which is at least 20 times higher that modulus of impedance of a said area of attached human tissue The system further includes impedance matching network (IMN) converting the impedance of treated area of human tissue into 50 Ohms in order to minimize reflected power from human tissue and provide a traveling wave through a human tissue.

The system further includes a phase shifting device at the input of the IMN providing an achievement of maximum of RF traveling-wave at a predetermined depth under the surface or on the surface.

According to another aspect of the present invention there is provided a method, which includes operation of the system.

According to further features in preferred embodiments of the invention described below the applicator is made from Al, Ag, Au, copper, or copper and aluminum alloys and coated with dielectric material.

According to still further features in the described preferred embodiments the applicator is made from Al coated by alumina.

According to still further features in the described preferred embodiments the applicator is moved on the surface of treated skin.

According to still further features in the described preferred embodiments the feeding cable connects RF-applicator and RF-resonator with impedance matching systems.

According to still further features in the described preferred embodiments the feeding cable has resonance $(n*\lambda/2)$ length where $\lambda$—is a wavelength of RF-energy in the cable material and n—is whole number According to still further features in the described preferred embodiments the impedance matching system provides compensation of the reactance of the attached piece of human tissue.

According to still further features in the described preferred embodiments the impedance matching system is fixed L, T or Π-shape structure.

According to still further features in the described preferred embodiments the impedance matching system is broadband impedance transformer.

According to still further features in the described preferred embodiments the impedance matching system is variable.

According to still further features in the described preferred embodiments the phase shifter is trombone type.

According to still further features in the described preferred embodiments the phase shifter is constructed of coaxial cable.

According to still further features in the described preferred embodiments the phase shift provided by the phase shifter is variable in time.

According to still further features in the described preferred embodiments the impedance meter (sensor) is inserted between matching system and RF-applicator.

According to still further features in the described preferred embodiments the said impedance matching system is controllable by feedback system obtaining the signal from the said impedance meter (sensor) for the purpose of reaching the optimal impedance matching and maximal energy deposition into human tissue.

According to still further features in the described preferred embodiments the coupled energy is delivered from RF-generator (amplifier).

According to still further features in the described preferred embodiments the delivered RF-power is coupled in continuous or pulsing mode.

According to still further features in the described preferred embodiments the control of the energy coupled to human tissue is achieved by variation of amplitude or duty cycle of RF-power in pulsing mode (PWM-control).

According to still further features in the described preferred embodiments the certain part of human body is in contact with second point of the said RF-resonator (for example ground).

According to still further features in the described preferred embodiments the operation is provided on the resonance frequency of human body.

According to still further features in the described preferred embodiments the treatment with RF-applicator t is combined with the laser treatment.

According to still further features in the described preferred embodiments the treatment with RF-applicator t is combined with ultrasonic treatment.

According to still further features in the described preferred embodiments the treatment with RF-applicator t is combined with UV-treatment According to still further features in the described preferred embodiments the treatment with RF-applicator t is combined with plasma treatment According to still further features in the described preferred embodiments the treatment with RF-applicator t is combined with flash-lamp treatment.

According to one aspect of the present invention there is provided an improved system for thermal treatment of a selected target within a subject, the system includes: (a) an RF energy source capable of producing an output RF power signal directed to an applicator contactable with a surface of a biological tissue belonging to the subject, the applicator capable of delivering a desired amount of energy to a predetermined energy dissipation zone beneath the surface of the biological tissue, the selected target positioned within the predetermined energy dissipation zone; (b) a phase shifter, the phase shifter capable of shifting a phase of directed traveling waves of the output signal so that energy therefrom is concentrated primarily in the predetermined energy dissipation zone, which lies at a desired depth beneath the surface of the biological tissue; (c) an impedance matching network (IMN), the IMN capable of converting the impedance of the biological tissue belonging to the subject from a nominal value to a corrected value, the corrected value matching an impedance characteristic of the RF transmission line so that the directed traveling wave may pass through the surface of the biological tissue without being converted to a standing wave; (d) an RF resonator located in the applicator, the RF resonator capable of cyclically accumulating and releasing the desired amount of energy, the RF resonator further capable of concentrating the desired amount of energy so that a significant portion thereof is concentrated in the predetermined energy dissipation zone; and (e) the applicator capable of conveying the output RF power signal from the RF energy source through the surface of the biological tissue to the predetermined energy dissipation zone after the output has been processed by the phase shifter, the IMN and the resonator. The absence of a ground electrode permits free propagation of the waves of the output RF power signal in the energy dissipation zone.

According to another aspect of the present invention there is provided an improved method for thermal treatment of a selected target within a subject. The method includes: (a) providing an output RF power signal directed to an applicator contactable with a surface of a biological tissue belonging to the subject, (b) employing a phase shifter to shift a phase of directed traveling waves of the output RF power so that energy therefrom is concentrated primarily in a predetermined energy dissipation zone which lies at a desired depth beneath the surface of the biological tissue, wherein the selected target is positioned within the predetermined energy dissipation zone; (c) converting the impedance of the biological tissue belonging to the subject from a nominal value to a corrected value, the corrected value matching an impedance characteristic of RF-transmission line so that the directed traveling wave may pass through the surface of the biological tissue without being converted to a standing wave by means of an impedance matching network (IMN); (d) cyclically accumulating in an RF resonator located in the applicator, and releasing therefrom, the desired amount of energy, (e) concentrating the desired amount of energy in the RF resonator so that a significant portion thereof is concentrated in the predetermined energy dissipation zone upon release therefrom; and (f) conveying the output signal of RF energy through the surface of the biological tissue to the predetermined energy dissipation zone after the output has been processed by the phase shifter, the IMN and the resonator by means of the applicator. The absence of a ground electrode permits free propagation of the waves in the output signal in the energy dissipation zone.

According to yet another aspect of the present invention there is provided an improved method for cellulite treatment. The method includes: (a) providing an output signal of RF energy directable to an applicator contactable with a surface of a biological tissue belonging to the subject, (b) employing a phase shifter to shift a phase of directed traveling waves of the output RF power so that energy therefrom is concentrated primarily in a predetermined energy dissipation zone which lies at a desired depth beneath the surface of the biological tissue, wherein the selected target is positioned within the predetermined energy dissipation zone, the predetermined energy dissipation zone including at least one cellulite body; (c) converting the impedance of the biological tissue belonging to the subject from a nominal value to a corrected value, the corrected value matching an impedance characteristic of RF-transmission line so that the directed traveling wave so that the output signal may pass through the surface of the biological tissue without being converted to a standing wave by means of an impedance matching network (IMN); (d) cyclically accumulating in an RF resonator located in the applicator, and releasing therefrom, the desired amount of energy, (e) concentrating the desired amount of energy in the RF resonator so that a significant portion thereof is concentrated in the predetermined energy dissipation zone upon release therefrom; and (f) conveying the output power from the RF energy source through the surface of the biological tissue to the predetermined energy dissipation zone after the output has been processed by the phase shifter, the IMN and the resonator by means of the applicator. The absence of a ground electrode permits free propagation of the waves in the output signal in the energy dissipation zone. The at least one cellulite body is heated to a greater degree than a tissue adjacent thereto.

According to further features in preferred embodiments of the invention described below, the system further includes a pulse width modulation (PWM)-controller, the PWM-controller capable of causing the RF energy source to deliver the output signal in pulses of a desired amplitude, a predetermined duration with a desired repetition frequency for average output power control.

According to still further features in the described preferred embodiments the system further includes a dielectric barrier positionable between the applicator and the surface of the biological tissue; the dielectric barrier preventing transmission of a conductive current.

According to still further features in the described preferred embodiments the applicator is made from at least one metal selected from the group consisting of aluminum, silver, gold, copper and alloys thereof.

According to still further features in the described preferred embodiments the dielectric barrier is supplied as a dielectric coating on the applicator.

According to still further features in the described preferred embodiments the applicator is constructed primarily of aluminum and the dielectric barrier is supplied as an alumina coating.

According to still further features in the described preferred embodiments the applicator is movable on the surface of the biological tissue as a means of altering a location of the energy dissipation zone.

According to still further features in the described preferred embodiments the system further includes a feeding cable, the feeding cable connecting the RF-applicator and the RF-resonator with the IMN.

According to still further features in the described preferred embodiments the feeding cable has a resonance length defined by $n*\lambda/2$ length, where $\lambda$ is a wavelength of RF-energy in the cable material and n is a whole number.

According to still further features in the described preferred embodiments the IMN includes a fixed structure characterized by a shape selected from the group consisting of L shaped, T shaped and Π-shaped structure.

According to still further features in the described preferred embodiments the IMN includes a broadband impedance transformer.

According to still further features in the described preferred embodiments the IMN is variable.

According to still further features in the described preferred embodiments the phase shifter includes a trombone type phase shifting mechanism. Trombone type phase shifters are well known to those of ordinary skill in the art and are described in detail at www.microwaves101.com/encyclopedia/phaseshifters.cfm which is fully incorporated herein by reference (see Appendix A).

According to still further features in the described preferred embodiments the phase shifter is at least partially constructed of coaxial cable.

According to still further features in the described preferred embodiments a phase shift provided by the phase shifter is variable.

According to still further features in the described preferred embodiments the energy delivered to the predetermined energy dissipation zone is coupled in continuous or pulsing mode. The RF-energy is produced in the form of sinusoidal signal that can be modulated by rectangular pulses with lower frequency by PWM controller)

According to still further features in the described preferred embodiments the RF-energy is characterized by a resonance frequency which matches a known natural resonance frequency of the selected target.

According to still further features in the described preferred embodiments the system further includes at least one additional component selected from the group consisting of a laser beam, an ultrasonic transducer, a WV light source, a plasma treatment device and a flash lamp.

According to still further features in the described preferred embodiments the providing indicates provision of the output signal in pulses of a predetermined duration with a desired frequency.

According to still further features in the described preferred embodiments the method further includes interposing a dielectric barrier between the applicator and the surface of the biological tissue. The dielectric barrier prevents transmission of a conductive current.

According to still further features in the described preferred embodiments the method further includes constructing the applicator primarily of aluminum. More preferably, the dielectric barrier is supplied as an alumina coating on an aluminum applicator.

According to still further features in the described preferred embodiments the method further includes moving the applicator with respect to the surface of the biological tissue as a means of altering a location of the energy dissipation zone.

According to still further features in the described preferred embodiments the method further includes employing a feeding cable to connect the RF-applicator and the RF-resonator with the IMN.

According to still further features in the described preferred embodiments the method further includes varying the phase shift provided by the phase shifter.

The present invention successfully addresses the shortcomings of the presently known configurations by providing an improved system and method for heating biological tissue via RF energy, which relies upon a single electrode and does not require a cooling system to prevent burning of skin.

Implementation of the method and system of the present invention involves performing or completing selected tasks or steps manually, automatically, or a combination thereof. Moreover, according to actual instrumentation and equipment of preferred embodiments of the method and system of the present invention, selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

BRIEF DESCRIPTION OF PREFERRED EMBODIMENTS

Figure 1:
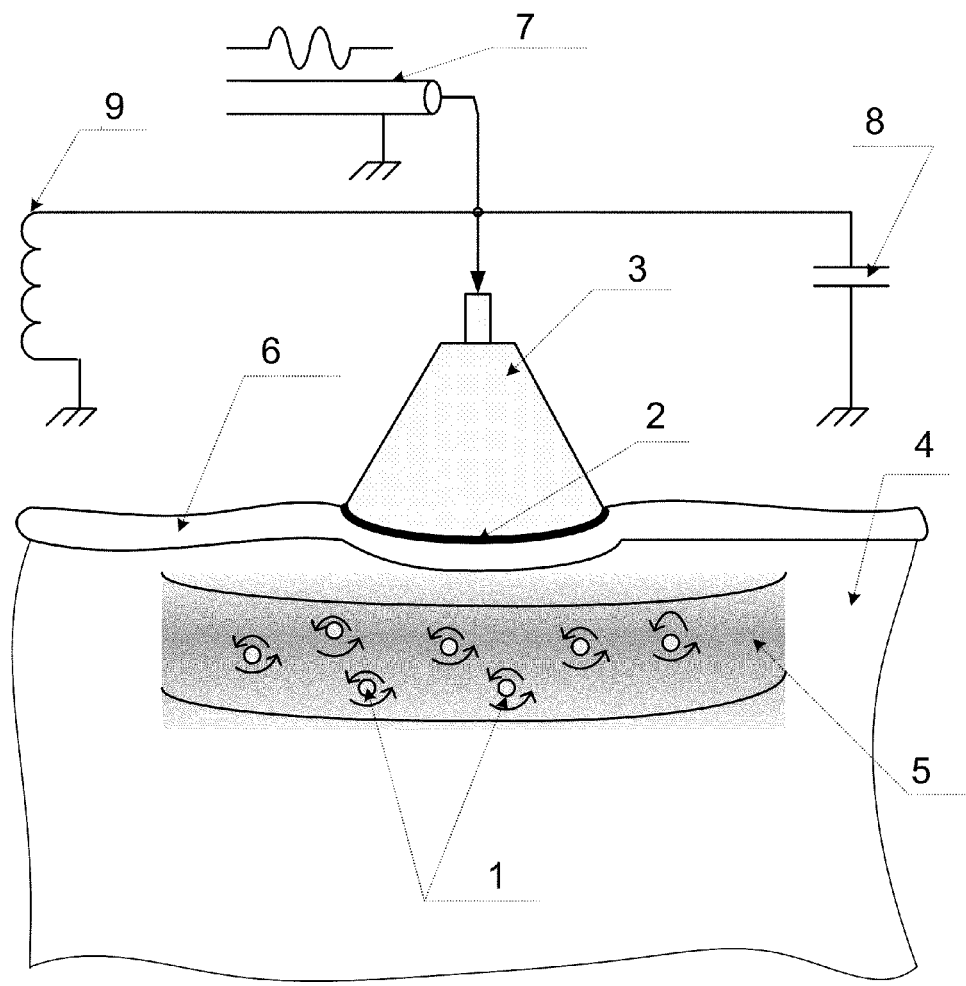
FIG. 1 is a simplified schematic diagram illustrating RF-power coupling to a treated tissue according to the present invention.

The present invention is of an improved system and method for heating biological tissue via RF energy, which requires only a single electrode.

Specifically, control of phase and pulse width modulation (PWM)-control of applied RF waves through the single electrode of the present invention obviate the need for cooling of the skin surface while facilitating efficient heating of underlying layers of tissue such as dermis and subcutaneous layers. As a result, the desired heating and contraction of adipose tissues is achieved. This allows, for the first time, non-invasive cellulite reduction.

The principles and operation of an improved system and method for heating biological tissue via RF energy according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. In addition, it is to be understood that the phraseology and terminology employed herein is for the purpose of description and should not be regarded as limiting.

The present invention offers several advantages with regard to previously available alternatives.

A single electrode, or applicator, employed without a ground electrode permits homogeneous application of RF-energy, which is directed primarily towards rotation, and vibration of dipole molecules, especially water molecules, in the applied electromagnetic wave.

Phase shifting techniques provide the possibility of concentration of RF-energy at a predetermined location by variation of position of RF-wave maximum Preferably, an Alumina-ceramic-coated applicator minimizes energy losses and prevents unwanted conductive current through human tissue.

A supporting parallel resonator attached in proximity to the applicator accumulates RF-energy and provides efficient excitation of the applicator and high RF-voltage on the application surface.

Application of high Kr-power in short-pulses provides fast and effective heating of cellulite capsules with relatively low average RF-power level.

PWM-control of output RF-power and simple IMN techniques provide good matching and low RF-power reflection with all types of human tissues. The additional advantage of applied fixed IMN and PWM-control ensure good impedance matching with variable types of human tissue without complicated impedance matching correction. The RF-applicator can be moved on the treated surface.

It will be appreciated that volumetric fatty tissue treatment requires deployment of a homogeneous RF-wave (through cross-section transversal to wave propagation) with maximum at a desired distance from the electrode-applicator. This homogeneous and high intensity RF-wave ensures efficient heating of cellulite capsules and fat cells because they retain water molecules. In contrast, blood and lymphatic vessels will not be subject to undesired heating because the natural circulation of water molecules in these vessels provides convective cooling. Further, blood and lymphatic vessels provide conductive cooling for other non-target tissues such as muscle, nerve tissue and connective tissue.

Referring now to the figures, principle components of a system according to the present invention and their operation are explained in greater detail.

Figure 2:
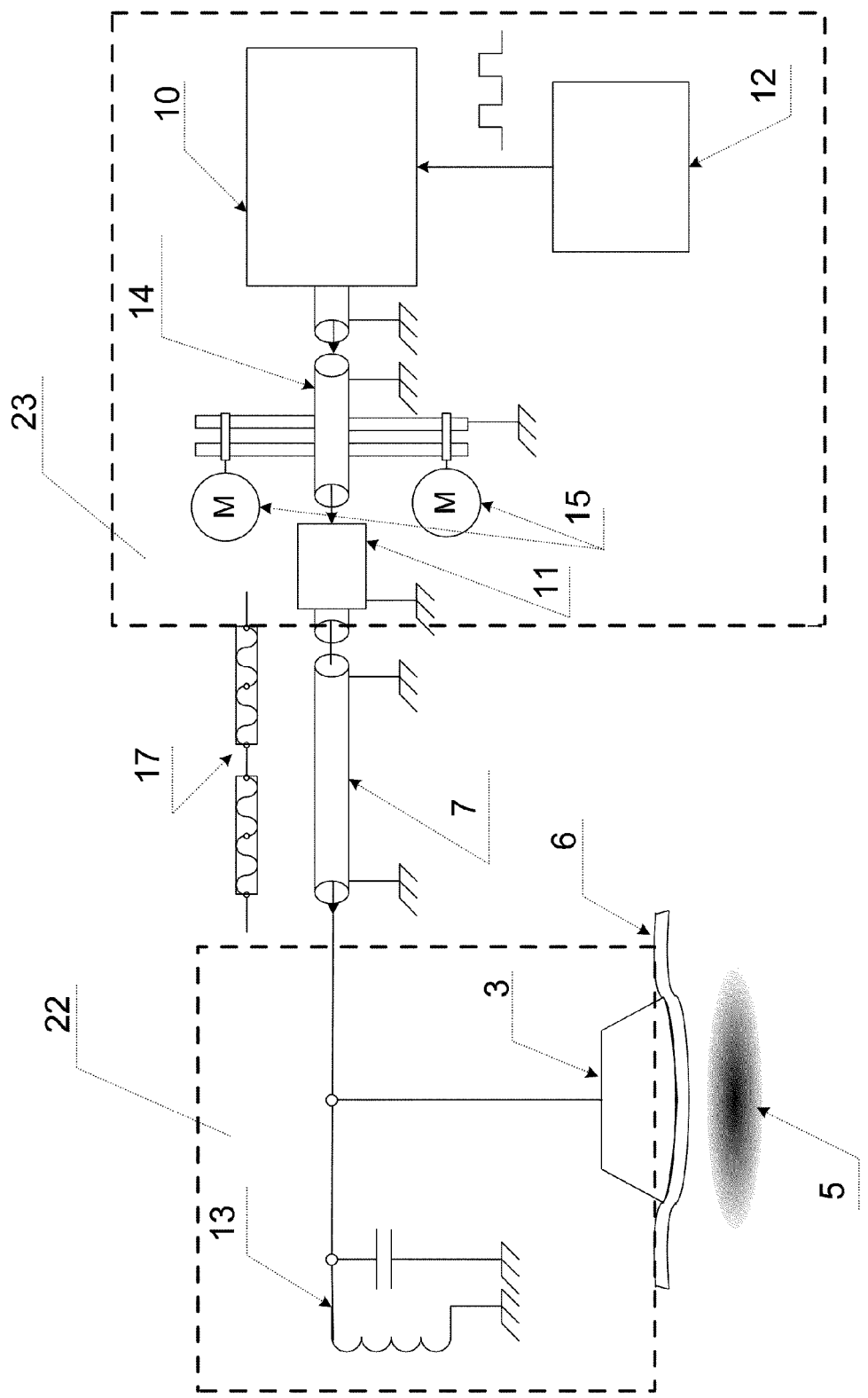
FIG. 2 is simplified schematic diagram of RF-system according to the present invention illustrating the principles of output power control with PWM and treating space control with phase shifting of incident RF-wave in accordance with a preferred embodiment of the present invention

The present invention is primarily embodied by a system 30 (FIGS. 1-3) for thermal treatment of a selected target within a subject. System 30 includes an RF energy source 10 capable of producing an output RF power signal 17 directed to an applicator 3 contactable with a surface 6 of a biological tissue 4 belonging to the subject. Applicator 3 is capable of delivering a desired amount of energy to a predetermined energy dissipation zone 5 beneath surface 6 of biological tissue 4. The selected target is positioned within the predetermined energy dissipation zone 5 and is represented in the figures as water molecules 1.

System 30 further includes a phase shifter (e.g. trombone-type phase shifter 14). Phase shifter 14 is capable of shifting a phase of directed traveling waves of output power 17 so that energy therefrom is concentrated primarily in the predetermined energy dissipation zone 5, which lies at a desired depth beneath surface 6 of biological tissue 4.

System 30 further includes an impedance matching network 11 (IMN capable of converting the impedance of biological tissue 4 belonging to the subject from a nominal value (e.g. 250-350 Ohms) to a corrected value (e.g. 50 Ohms). The corrected value matches an impedance characteristic of RF energy source and RF transmission line including phase shifter 14 and cable 11, so that output RF traveling wave 17 may pass through surface 6 of biological tissue 4 without being converted to a standing wave.

System 30 further includes an RF resonator 13 located in applicator 3, RF resonator 13 is capable of cyclically accumulating and releasing the desired amount of energy and is further capable of concentrating the desired amount of energy so that a significant portion thereof may be transmitted to predetermined energy dissipation zone 5.

System 30 further includes applicator 3 capable of conveying output RF power signal 17 from the RF energy source 10 through surface 6 of biological tissue 4 to predetermined energy dissipation zone 5 after output 17 has been processed by the phase shifter 14, IMN 11 and resonator 13.

Typically, operation of system 30 results in 2 to 4% loss of energy from output signal 17 with an additional 2-4% reflection of energy from output signal 17. This means that system 30 can reliably deliver 90-95% of energy from output signal 17 into zone 5. Neither concentration of energy from output signal 17 into a small zone 5, nor this degree of efficiency, were achievable with previously available alternatives. IMN 11 reduces reflection of applied output signal 17 from surface 6 thereby increasing efficiency of delivery of energy to energy dissipation zone 5.

Further, the absence of a ground electrode from system 30 permits free propagation of the waves of output RF power signal 17 in energy dissipation zone 5.

These factors serve to greatly increase the degree of heating of water molecules 1 relative to the degree of heating of water molecules 1 achieved with prior art alternatives.

Figure 4:
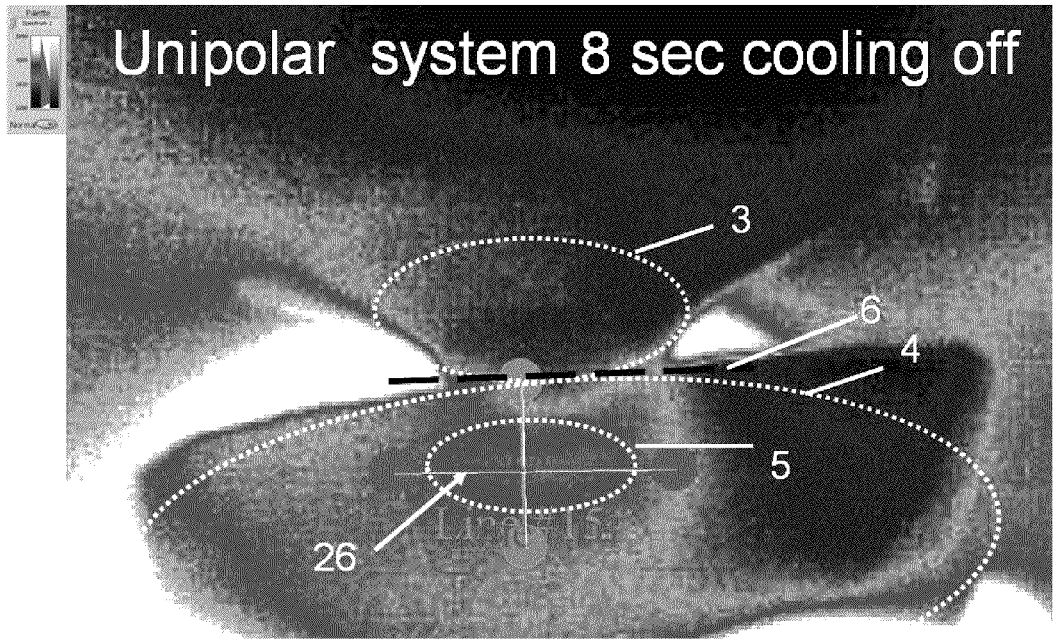
FIG. 4 is a thermo-gram illustrating heat distribution resulting from operation of a system according to the present invention using a slice of an apple as a target.
Figure 5:
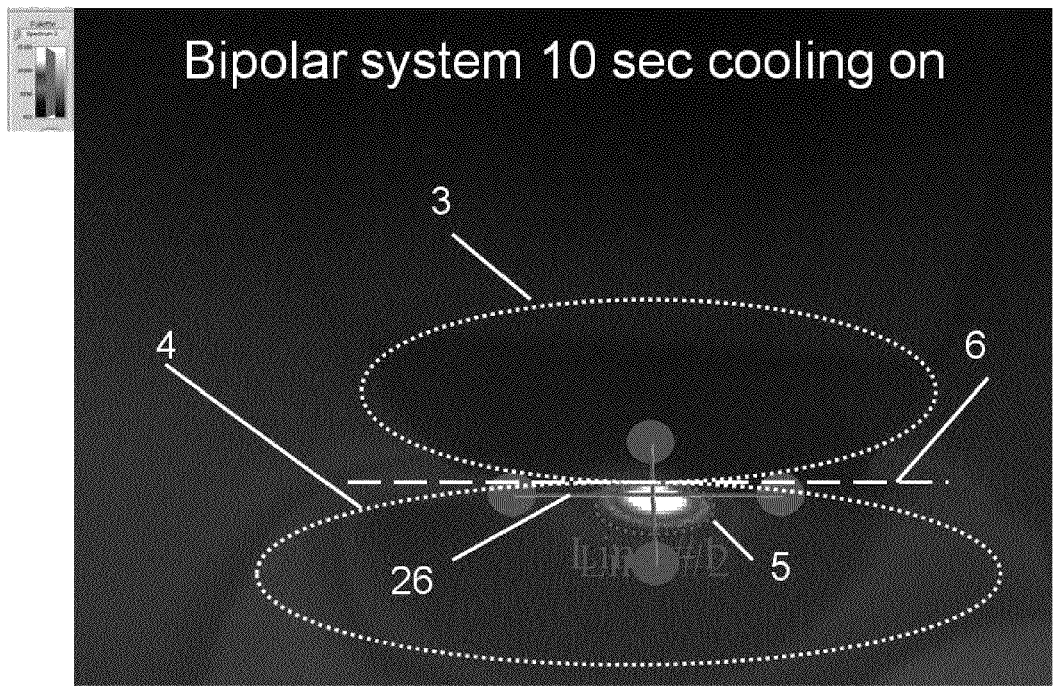
FIG. 5 is a thermo-gram illustrating heat distribution resulting from operation of a prior art system according to the present invention using a slice of an apple as a target.
Figure 6:
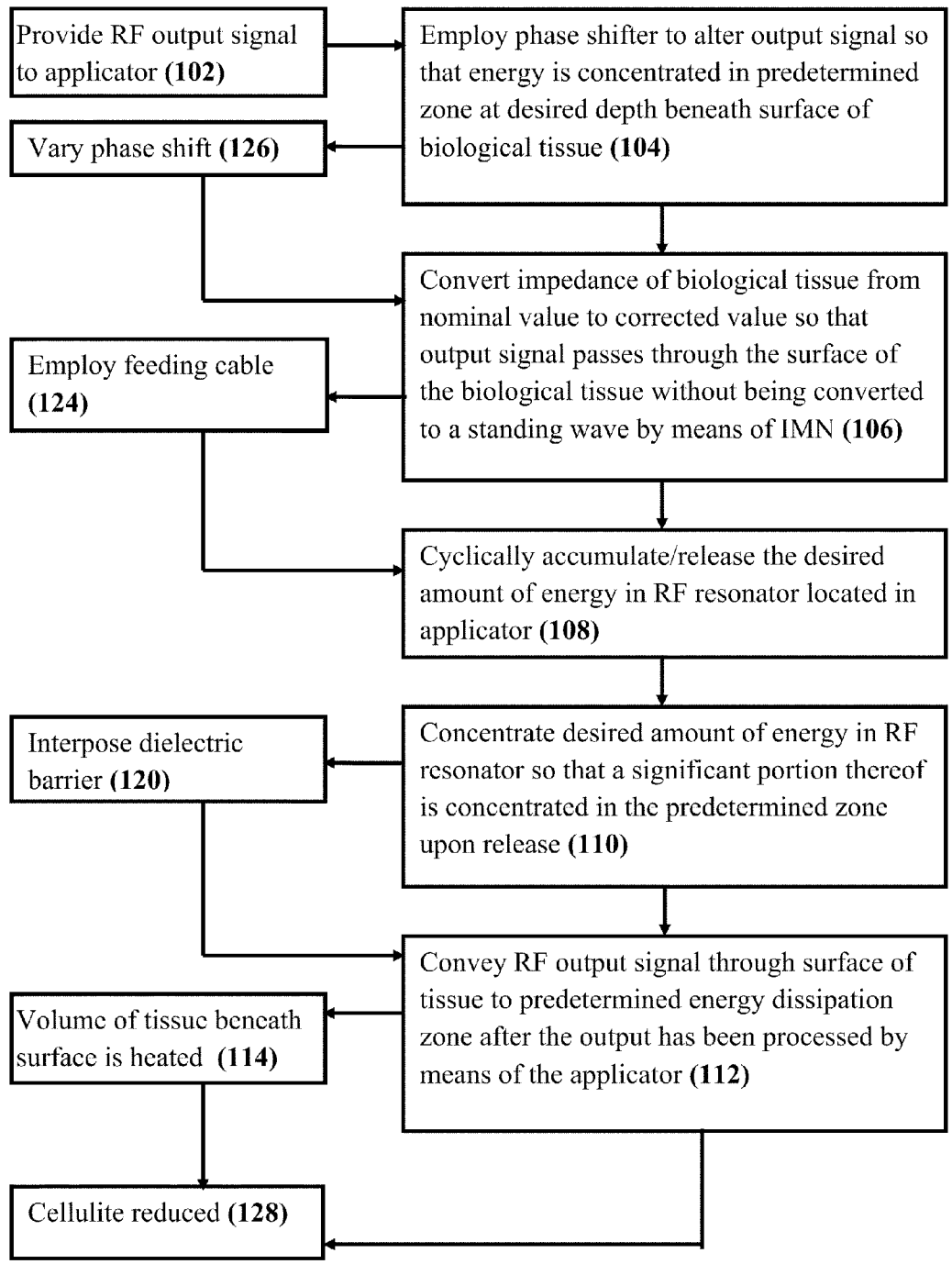
FIG. 6 is a simplified flow diagram illustrating a sequence of events associated with performance of a method according to the present invention.

The inherent advantages of system 30 are clear from comparison of thermo-grams of energy dissipation zone 5 using system 30 (FIG. 4) and a prior art bipolar (i.e. 2 electrode) system (FIG. 5). Each thermo-gram is accompanied by a key on the left which indicates that the colors white, yellow, orange, red, green, blue and violet represent concentrations of heat energy in decreasing order. In each figure, an apple slice is used as biological tissue 4.

FIG. 4 clearly shows that when applicator 3 of system 30 is contacted with surface 6 of tissue 4, delivery of output energy 17 results in delivery of energy primarily to zone 5. Line 26 passes through the center of zone 5.

In sharp contrast, FIG. 5 clearly shows that when applicator 3 of a prior art bipolar system is contacted with surface 6 of tissue 4, delivery of output energy 17 results in delivery of energy primarily to a zone 5 which is adjacent to surface 6 of tissue 4. This reduces the distance between line 26, which passes through the center of zone 5, and surface 6. In other words, the prior art bipolar system delivers heat energy primarily in proximity to surface 6. The thermo-gram of FIG. 5 illustrates a distribution of heat energy observed when the prior art bipolar system is operated with a cooling system.

Optionally, but preferably, system 30 further includes a PWM controller, the PWM controller 12 capable of causing the RF energy source to deliver the output power signal in pulses of a predetermined duration and amplitude with a desired frequency. For example, the operating RF-frequency is 40.68 MHz, a PWM-frequency is 1 to 20 kHz and a duty cycle is 10 to 90%.

According to some preferred embodiments of the invention, applicator 3 is made from metals such as, for example, aluminum, silver, gold, copper or alloys thereof. Alternately, or additionally, a dielectric barrier 2 may be positioned between applicator 3 and surface 6 of biological tissue 4. Dielectric barrier 2 prevents unwanted transmission of a conductive current to tissue 4. According to some preferred embodiments of the invention, dielectric barrier 2 is supplied as a dielectric coating on applicator 3. According to a most preferred embodiment, applicator 3 is constructed primarily of aluminum and dielectric barrier 2 is supplied as an alumina coating.

Optionally, but preferably, applicator 3 is movable on surface 6 of biological tissue 4 as a means of altering a location of energy dissipation zone 5.

Optionally, but preferably, system 30 further includes a feeding cable 7, the feeding cable 7 connecting RF-applicator 3 and the RF-resonator 13 with IMN 11. Optionally, but preferably, feeding cable 7 has a resonance length defined by n*λ/2 length, where λ is a wavelength of RF-energy in the cable material and n is a whole number.

Optionally, but preferably, IMN 11 includes a fixed structure characterized by a shape such as, for example, L shaped, T shaped or Π-shaped structure. Optionally, but preferably, IMN 11 includes a broadband impedance transformer. Optionally, but preferably, IMN 11 is variable.

Optionally, but preferably, phase shifter 14 includes a trombone type phase shifting mechanism.

Alternately, or additionally, phase shifter 14 may be at least partially constructed of coaxial cable.

Optionally, but preferably, phase shifter 14 provides a variable phase shift.

Optionally, but preferably, RF-generator 10 delivers coupled energy.

Optionally, but preferably, the energy delivered to the predetermined energy dissipation zone 5 is coupled in a continuous or a pulsing mode. RV-generator 10 produces output 17 in the form of a sinusoidal signal which may be modulated by rectangular pulses with lower frequency. This may be accomplished, for example, by PWM controller 12.

According to one most preferred embodiment of the invention, system 30 employs RF-energy 17 which is characterized by a resonance frequency that matches a known natural resonance frequency of the selected target.

Optionally, but preferably, system 30 may further include additional components, such as, for example, a laser beam, an ultrasonic transducer, a UV light source, a plasma treatment device and a flash lamp.

The present invention is further embodied by an improved method 100 for thermal treatment of a selected target within a subject. Method 100 includes: providing 102 output RF power signal 17 directed to applicator 3 contactable with surface 6 of biological tissue 4 belonging to the subject.

Method 100 includes employing 104 a phase shifter 14 to shift a phase of RF-traveling waves of output RF power 17 so that energy therefrom is concentrated primarily in predetermined energy dissipation zone 5 which lies at a desired depth beneath surface 6 of biological tissue 4. The selected target is positioned within energy dissipation zone 5.

Method 100 further includes converting 106 impedance of biological tissue 4 belonging to the subject from a nominal value to a corrected value. The corrected value matches a characteristic impedance characteristic of RF energy source and RF transmission line including a cable II and a phase shifter 14 so that output RF-traveling wave 17 may pass through surface 6 of biological tissue 4 without being converted to a standing wave by means of IMN 11;

Method 100 further includes cyclically 108 accumulating/releasing in an RF resonator 13 located in applicator 3 the desired amount of energy.

Method 100 further includes concentrating 110 the desired amount of energy in RF resonator 13 so that a significant portion thereof is concentrated in the predetermined energy dissipation zone 5 upon release from resonator 13.

Method 100 further includes conveying 112 output 17 from RF energy source 10 through surface 6 of biological tissue 4 to predetermined energy dissipation zone 5 after output 17 has been processed by the phase shifter 14, the IMN 11 and resonator 13 by means of applicator 3.

The absence of a ground electrode permits free propagation of the waves in output signal 17 in energy dissipation zone 5.

According to still further features in the described preferred embodiments the providing indicates provision 118 of output signal 17 in pulses of a predetermined duration and an amplitude with a desired frequency as detailed hereinabove.

Preferably, method 100 further includes interposing 120 a dielectric barrier 2 between applicator 3 and surface 6 of biological tissue 4. Dielectric barrier 2 prevents transmission of a conductive current. Preferably, method 100 further includes constructing applicator 3 primarily of aluminum. More preferably, dielectric barrier 2 is supplied as an alumina coating on an aluminum applicator 3.

Preferably, method 100 further includes moving 122 applicator 3 with respect to surface 6 of biological tissue 4 as a means of altering a location of energy dissipation zone 5.

Optionally, but preferably, method 100 further includes employing 124 a feeding cable 7 to connect applicator 3, and resonator 13 with IMN 11.

Optionally, but preferably, method 100 further includes varying 126 the phase shift provided by phase shifter 14.

Method 100 is optimally employed for cellulite treatment by selecting a predetermined energy dissipation including at least one cellulite body which serves as a target which is heated to a greater degree than tissue adjacent thereto. As a result, cellulite is reduced 128.

The present invention relies upon RF-heating of biological tissues via rotation of molecules of the water molecules 1 (FIG. 1), which are dipole structures, in an alternating electromagnetic field. In order to avoid a conductive HF-current a dielectric barrier 2 provides insulation between the applicator 3 and a biological tissue surface 6.

Preferably, applicator 3 is constructed from aluminum or an aluminum alloy covered by alumina coating with a thickness 40-50 µm.

Applicator 3 can be also described as an antenna coupler that irradiates the RF-wave into deep tissue 4. The resultant dissipation of the energy load can be described as irradiative coupling of RF-energy.

The area through which applied RF energy is primarily applied 5 is determined by the contact area between tissue surface 6 and applicator 3 and by the phase of incident electromagnetic wave pulses 17. The energy diverges from surface 6 and is effectively dissipated 5 through tissue 4. The depth of RF-energy penetration depends on RF-power and area of applicator and phase shift of electromagnetic wave. By application of phase shifting device 14 it is possible to adjust a position of energy dissipation zone 5 and to coincide with a selected target (e.g. cellulite lesions).

The applied oscillating RF-field stimulates all dipole molecules (mostly water molecules 1) to rotate and vibrate with consequent heating of energy dissipation zone 5. Zone 5 may be controlled by phase shifting device 14 between RF-generator 10 and applicator 3. Heating will be primarily in adipose tissue because it is rich in liquids but not subject to convective cooling as blood vessels are. The pulse width modulation (PWM) control 12 of output RF-power that provide a possibility to keep a high peak RF-power with low average power level.

The absence of a second or ground electrode in the pictured configuration permits free propagation of RF waves inside tissue 4.

In order to maximize transmission of RF-energy from RF-source 10 (FIG. 2) through resonant cable 7 to applicator 3, it is connected to the central point of a parallel resonator 13 including a capacitor 8 and an inductor 9 connected in parallel and characterized by very high-Q-factor for example more than 20.

The delivered oscillating RF-power (e.g. 25-300 watts) is stored in the resonator 13 therefore an active (dissipative) load of resonator 13 is only an adjacent tissue.

The active losses of resonator 13 are very low (20-50 times less than energy dissipated inside tissue 4). The intermittent discharges of capacitor 8 and the inductor 9 are coupled through applicator 3 to tissue 4.

RF-generator 10 capable of producing 200-400 Watts full power at 40.68 MHz operating frequency demonstrates an optimal performance at 50 Ohms resistive load. Optimal performance means minimal reflected RF-power with maximum RF-forward power dissipated by a load. Thus, the real load that includes treated volume 5 of tissue 4 is matched as 50 Ohms load.

The used impedance matching network (IMN 11; see FIG. 2) is fixed (the elements are not variable operatively); therefore operation occurs without RF-power amplitude changes. The control of output power is reached by PWM-control (pulse width modulation). PMW achieves modulation of output power by rectangular power pulses applied with a frequency lower than that of the RF wave. In order to decrease RF-power coupling it is necessary to reduce a duty cycle of PWM. PWM-controller 12 produces rectangular pulses with a modulation frequency range of 2-10 kHz. The duty cycle may be varied from 5 to 100%. The shape of RF-power pulse 17 is showed in FIG. 2. The PWM-control of output RF-power permits high peak RF-power level in heating zone 5 with lower average power. This provides efficient heating of adipose capsules with minimal impact on blood vessels and other tissues.

The reflected RF-power is 1-2% of output power therefore 98% of output power is dissipated in the treated volume. Typically, we concentrate energy in adipose tissue therefore coupled RF-energy is dissipated by fat cells, cellulite capsules and by blood and lymphatic liquids. The energy that produces a useful job in fat cells and cellulite tissue will reach 70-80% of total energy coupled to the volume. The rest energy is dissipated through diffusion of the heat to the surface and by convection of natural liquids of human body.

Applicator 3 is connected to parallel resonator 13. Applicator 3 and resonator 13 are physically positioned inside of operating hand-piece 22 used for treatment procedure. The IMN-system locates inside the main system 23. In order to avoid a mismatching phase shift between the applicator 3 and the IMN 11, the length of cable 7 is equal to the whole number (n) of wavelength of RF-energy ($\lambda$) in the cable material.

In order to reach necessary amplitude under the surface 6 of tissue 4, a phase shifting system (e.g. trombone-type system 14) is inserted between output of RF-generator 10 and an input of IMN 11. The position of the maximum of energy dissipation can be controlled by this phase shifting system. In order to control the depth of RF-energy penetration the length of trombone can be shortened that change a position of dissipated electromagnetic wave in the tissue or an area of the maximum of RF-voltage. Consequently, RF-energy will be dissipated most efficiently in the volume around maximum of the RF-voltage.

The phase shifter 14 can be controlled automatically, for example by motors 15. This change of phase could be linear or periodical that provides a displacement of maximal heating zone inside the tissue or scanning of maximal heating zone position.

Figure 3:
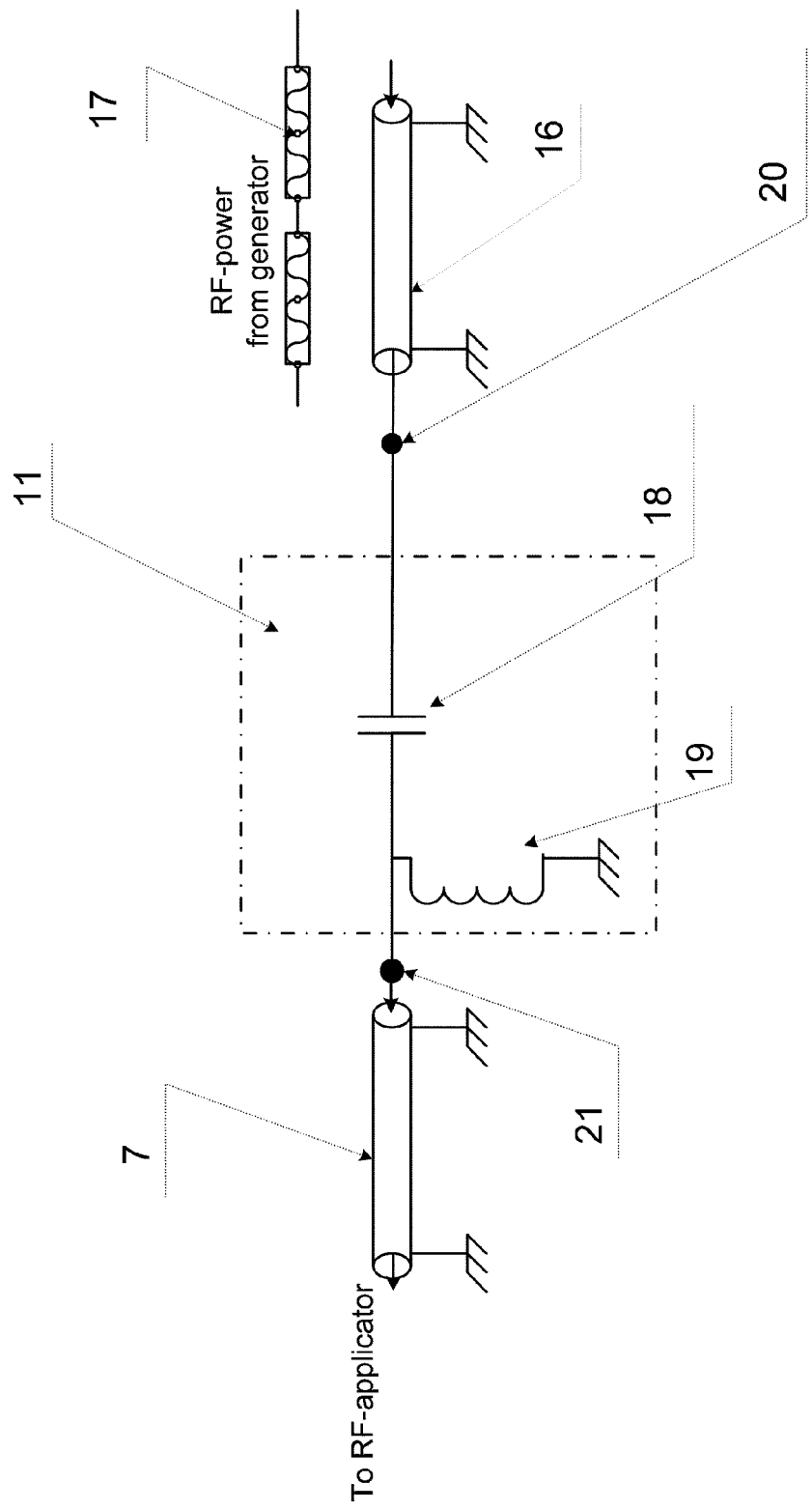
FIG. 3 illustrates an impedance matching system in accordance with the present invention.

The practical implementation of impedance matching system 11 is illustrated by FIG. 3. The RF-power delivered from RF-generator 10 through coaxial cable 16 is modulated by rectangular pulses 17. Because RF-generator 10 is matched to 50 Ohms and impedance of human tissue is close to 300 Ohms, it is necessary to convert 50 to 300 Ohms with compensation of electromagnetic reactance of tissue 4. This is achieved with impedance matching network 11. L-type simple fixed IMN consisting of R-capacitor IS and RF-inductor 19 (FIG. 3) were applied for this purpose. Half-wave cable 7 is applied for transmission of RF-energy from IM 11 to RF applicator 3 without phase shifting that is controllable by phase shifting system. The measured impedance in the point 20 is 50 Ohms and in the point 21 is 300 Ohms. Impedance matching networks of various types may be employed without significantly altering performance of the present invention. Regardless of the exact INN type employed, the IMN 11 can be variably and/or automatically controlled to trace an impedance changing.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. An improved system for thermal treatment of a selected target within a subject, the system comprising:
    (a) an electromagnetic (EM) energy source capable of producing an output EM power signal directed to an applicator contactable with a surface of a biological tissue belonging to the subject, said applicator capable of delivering a desired amount of energy to a predetermined energy dissipation zone beneath said surface of said biological tissue, the selected target positioned within said predetermined energy dissipation zone;
    (b) a phase shifter, said phase shifter capable of shifting a phase of EM waves of said output EM signal so that energy therefrom is concentrated primarily in said predetermined energy dissipation zone, which lies at a desired depth beneath said surface of said biological tissue;
    (c) an electromagnetic (EM) resonator, said EM resonator capable of cyclically accumulating and releasing said desired amount of energy, said EM resonator further capable of concentrating said desired amount of energy so that a significant portion thereof is concentrated in said predetermined energy dissipation zone; and
    (d) said applicator capable of conveying said output EM power signal from said EM energy source through said surface of said biological tissue to said predetermined energy dissipation zone after said output has been processed by said phase shifter and said resonator;
    wherein the absence of a ground electrode permits free propagation of said waves of said output EM power signal in said energy dissipation zone.

2. The system of claim 1, further comprising a pulse width modulation controller, said pulse width modulation controller capable of causing said EM energy source to deliver said output signal in pulses of a predetermined duration and amplitude with a desired frequency.

3. The system of claim 1 wherein said resonator is connected to said applicator.

4. The system of claim 1 wherein said resonator is located within said applicator.

5. The system of claim 1 wherein the EM energy source is a radio frequency (RF) energy source and the EM power signal is an RF power signal.

6. The system of claim 1 wherein
    the system further comprises an impedance matching network (IMN) configured to reduce reflection of output RF power from a surface of biological tissue to the electromagnetic (EM) energy source.

7. The system of claim 6, further comprising a feeding cable, said feeding cable connecting said applicator and said EM resonator with said IMN.

8. The system of claim 7, wherein said feeding cable has a resonance length defined by n*λ/2 length, where λ is a wavelength of EM-energy in the cable material and n is a whole number.

9. The system of claim 6, wherein the system is configured so that at least one of a first condition, a second condition and a third condition is true, and the first, second and third conditions are defined as follows:
   i) according to said first condition, said IMN includes a fixed structure characterized by a shape selected from the group consisting of L shaped, T shaped and Π-shaped structure;
   ii) according to said second condition, said IMN includes a broadband impedance transformer; and
   iii) according to said third condition, said IMN is variable.

10. The system of claim 1, further comprising a dielectric barrier positionable between said applicator and said surface of said biological tissue; said dielectric barrier preventing transmission of a conductive current, wherein the system is configured so that at least one of a first condition and a second condition is true and the first and second conditions are defined as follows:
   i) according to the first condition, said dielectric barrier is supplied as a dielectric coating on said applicator; and
   ii) according to the second condition, said applicator is constructed primarily of aluminum and said dielectric barrier is supplied as an alumina coating.

11. The system of claim 1, wherein said applicator is movable on said surface of said biological tissue as a means of altering a location of said energy dissipation zone.

12. The system of claim 1, wherein the system is configured so that at least one of a first condition, a second condition and a third condition is true, and the first, second and third conditions are defined as follows:
   i) according to said first condition, said phase shifter includes a trombone type;
   ii) according to said second condition, said phase shifter is at least partially constructed of coaxial cable; and
   iii) according to said third condition, a phase shift provided by said phase shifter is variable.

13. The system of claim 1, said EM energy source is configured to deliver coupled energy.

14. The system of claim 1, wherein said system is configured such that said energy delivered to said predetermined energy dissipation zone is coupled in continuous or pulsing mode.

15. The system of claim 1, wherein said EM-energy is characterized by a resonance frequency which matches a known natural resonance frequency of the selected target.

16. The system of claim 1 wherein the system is configured to heat said volume of said biological tissue beneath said surface so that said volume of said biological tissue is maintained at a lower temperature than said predetermined energy dissipation zone without a cooling device.

17. The system of claim 1, further comprising at least one additional component selected from the group consisting of a laser beam, an ultrasonic transducer, a UV light source, a plasma treatment device and a flash lamp.

18. An improved method for thermal treatment of a selected target within a subject, the method comprising:
   (a) providing an output EM power signal directed to an applicator contactable with a surface of a biological tissue belonging to the subject,
   (b) employing a phase shifter to shift a phase of EM waves in said output EM power signal so that energy therefrom is concentrated primarily in a predetermined energy dissipation zone which lies at a desired depth beneath said surface of said biological tissue, wherein the selected target is positioned within said predetermined energy dissipation zone;
   (c) cyclically accumulating in an EM resonator and releasing therefrom, a desired amount of energy,
   (d) concentrating said desired amount of energy in said EM resonator so that a significant portion thereof is concentrated in said predetermined energy dissipation zone upon release therefrom; and
   (f) conveying said output signal of EM energy through said surface of said biological tissue to said predetermined energy dissipation zone after said output has been processed by said phase shifter, and said resonator wherein the absence of a ground electrode permits free propagation of said waves in said output signal in said energy dissipation zone.

19. The method of claim 18, wherein said providing of said EM output signal includes provision of said output signal in pulses of a predetermined duration and amplitude with a desired frequency.

20. The method of claim 18 wherein said resonator is connected to said applicator.

21. The method of claim 18 wherein said resonator is located within said applicator.

22. The method of claim 18 wherein the EM energy source is a radio frequency (RF) energy source and the EM power signal is an RF power signal.

23. The method of claim 18 wherein:
   (i) the method further comprises the step of converting the impedance of said biological tissue belonging to the subject from a nominal value to a corrected value by means of an impedance matching network (IMN) in order to reduce reflection of EM power from a surface of the biological tissue; and
   (ii) said output EM power signal that is conveyed through said surface of said biological tissue to said predetermined energy dissipation zone is processed by said IMN.

24. The method of claim 23, further comprising employing a feeding cable to connect said applicator and said resonator with said IMN.

25. The method of claim 24, wherein said feeding cable has a resonance length defined by n*λ/2 length, where λ is a wavelength of EM-energy in the cable material and n is whole number.

26. The method of claim 23, wherein the method is carried out so that at least one of a first condition, a second condition and a third condition is true, and the first, second and third conditions are defined as follows:
   i) according to said first condition, said IMN includes a fixed structure characterized by a shape selected from the group consisting of L shaped, T shaped and Π-shaped structure;
   ii) according to said second condition, said IMN includes a broadband impedance transformer; and
   iii) according to said third condition, said IMN is variable.

27. The method of claim 18, further comprising interposing a dielectric barrier between said applicator and said surface of said biological tissue; said dielectric barrier preventing transmission of a conductive current.

28. The method of claim 27, wherein the method is carried out so that at least one of a first condition and a second condition is true, and the first, and second conditions are defined as follows:
  i) according to the first condition, said dielectric barrier is supplied as a dielectric coating on said applicator; and
  ii) according to the second condition, said applicator is constructed primarily of aluminum and said dielectric barrier is supplied as an alumina coating.

29. The method of claim 18, further comprising moving said applicator with respect to said surface of said biological tissue as a means of altering a location of said energy dissipation zone.

30. The method of claim 18, wherein the method is carried out so that at least one of a first condition, a second condition and a third condition is true, and the first, second and third conditions are defined as follows:
  i) according to said first condition, said phase shifter includes a trombone type;
  ii) according to said second condition, said phase shifter is at least partially constructed of coaxial cable; and
  iii) according to said third condition, a phase shift provided by said phase shifter is variable.

31. The method of claim 18, wherein said provided output signal of EM energy is indicative of coupled energy.

32. The method of claim 18, wherein said energy delivered to said predetermined energy dissipation zone is coupled in continuous or pulsing mode.

33. The method of claim 18, wherein said desired amount of energy released by said EM resonator is characterized by a resonance frequency that matches a known resonance frequency of the selected target.

34. The method of claim 18, wherein (a) through (e) are performed in the order listed.

35. The method of claim 18 wherein:
  i) said predetermined energy dissipation zone includes at least one cellulite body;
  ii) the method is carried out so that said at least one cellulite body is heated to
  a greater degree than a tissue adjacent thereto.

36. The method of claim 18 wherein the method is carried out to heat a volume of said biological tissue beneath said surface so that said surface of said biological tissue is maintained at a lower temperature than said predetermined energy dissipation zone without a cooling device.

37. The method of claim 18 wherein said applicator is made from at least one metal selected from the group consisting of aluminum, silver, gold, copper and alloys thereof.

* * * * *